(12) United States Patent
Amari et al.

(10) Patent No.: US 11,642,288 B2
(45) Date of Patent: May 9, 2023

(54) SKIN EXTERNAL COMPOSITION

(71) Applicant: KAO CORPORATION, Tokyo (JP)

(72) Inventors: Naomi Amari, Haga-gun (JP); Takuji Kume, Nara (JP); Makoto Onoo, Mitaka (JP); Takehiko Tojo, Utsunomiya (JP); Rui Takahashi, Suginami-ku (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 17/633,499

(22) PCT Filed: Feb. 5, 2021

(86) PCT No.: PCT/JP2021/004277
§ 371 (c)(1),
(2) Date: Feb. 7, 2022

(87) PCT Pub. No.: WO2021/157688
PCT Pub. Date: Aug. 12, 2021

(65) Prior Publication Data
US 2022/0287923 A1 Sep. 15, 2022

(30) Foreign Application Priority Data

Feb. 7, 2020 (JP) .............................. JP2020-020136
Feb. 3, 2021 (JP) .............................. JP2021-015623

(51) Int. Cl.
| | | |
|---|---|---|
| A61K 8/04 | (2006.01) | |
| A61K 8/73 | (2006.01) | |
| A61K 8/81 | (2006.01) | |
| A61Q 19/00 | (2006.01) | |
| A61K 8/02 | (2006.01) | |
| A61K 8/49 | (2006.01) | |
| A61K 8/63 | (2006.01) | |
| A61K 8/68 | (2006.01) | |
| A61K 9/00 | (2006.01) | |
| A61K 47/32 | (2006.01) | |
| A61K 47/36 | (2006.01) | |

(52) U.S. Cl.
CPC .............. *A61K 8/027* (2013.01); *A61K 8/04* (2013.01); *A61K 8/498* (2013.01); *A61K 8/63* (2013.01); *A61K 8/68* (2013.01); *A61K 8/73* (2013.01); *A61K 8/8129* (2013.01); *A61K 8/8176* (2013.01); *A61K 9/0014* (2013.01); *A61K 47/32* (2013.01); *A61K 47/36* (2013.01)

(58) Field of Classification Search
None
See application file for complete search history.

(56) References Cited

U.S. PATENT DOCUMENTS

| | | | |
|---|---|---|---|
| 2003/0215522 A1* | 11/2003 | Johnson | ................ A61P 17/00 424/642 |
| 2004/0131673 A1 | 7/2004 | Coffee et al. | |
| 2004/0265371 A1 | 12/2004 | Looney et al. | |
| 2010/0217170 A1 | 8/2010 | Tsuru et al. | |
| 2011/0136669 A1* | 6/2011 | Liebmann | .............. A01N 25/10 424/443 |
| 2012/0021026 A1* | 1/2012 | Glenn, Jr. | .............. D04H 1/728 424/59 |
| 2013/0125912 A1 | 5/2013 | Tojo et al. | |
| 2014/0045695 A1 | 2/2014 | Liebmann et al. | |
| 2016/0038611 A1 | 2/2016 | Vile et al. | |
| 2021/0069122 A1 | 3/2021 | Stranska et al. | |

FOREIGN PATENT DOCUMENTS

| | | |
|---|---|---|
| CN | 101327182 A | 12/2008 |
| CN | 102176904 A | 9/2011 |
| CN | 102808287 A | 12/2012 |
| CN | 103445973 A | 12/2013 |
| CN | 103614863 A | 3/2014 |
| CN | 105246469 A | 1/2016 |
| CN | 107881645 A | 4/2018 |
| EP | 3 290 059 A1 | 3/2018 |
| JP | 10-298108 A | 11/1998 |
| JP | 2004-531301 A | 10/2004 |
| JP | 2005-015484 A | 1/2005 |
| JP | 2011-530491 A | 12/2011 |
| JP | 2012-12714 A | 1/2012 |
| JP | 2013-532171 A | 8/2013 |
| JP | 2014-55119 A | 3/2014 |

(Continued)

OTHER PUBLICATIONS

Jiang Yongnan, et al., "Preparation of Epimedium Flavone PVP Drug-loaded Nanofibrous Membrane by Electrospinning", Journal of Chinese Medicinal Materials vol. 34 No. 12, Dec. 25, 2011, p. 1955-1958 (with machine translation of abstract).

(Continued)

*Primary Examiner* — Brian Gulledge
(74) *Attorney, Agent, or Firm* — Oblon, McClelland, Maier & Neustadt, L.L.P.

(57) ABSTRACT

Provided is a liquid skin external composition which allows a poorly water-soluble component to be applied to a skin in a liquid state.

An assembly of fiber for use in production of a liquid skin external composition, the assembly of fiber comprising (a) a polymer soluble in water and an alcohol or a ketone in a content of 50 mass % or more and 98 mass % or less with respect to the whole assembly of fiber and (b) a poorly water-soluble component in a content of 2 mass % or more and 40 mass % or less with respect to the whole assembly of fiber.

20 Claims, 2 Drawing Sheets

(56) References Cited

FOREIGN PATENT DOCUMENTS

| | | |
|---|---|---|
| JP | 2019-504075 A | 2/2019 |
| KR | 101411673 B1 | 6/2014 |
| WO | WO 2020/179907 A1 | 9/2020 |

OTHER PUBLICATIONS

Yu Deng-guang, et al., "The improvement of poorly water-soluble drug solubility through electrospun drug-loaded nanofibers", Acta Pharmaceutica Sinica, 44(10), Oct. 12, 2009, pp. 1179-1182 (including English abstract of p. 1179).
Yu Deng-guang, et al., "Improving effects of electospun composite nanofibers on the dissolution and pereation of poorly water soluble drugs", Functional Material, 3(41) Dec. 20, 2010, pp. 469-472 (including English abstract of p. 472).
Written Opinion dated Apr. 6, 2021, in PCT/JP2021/004277 (with English partial translation).
International Search Report dated Apr. 6, 2021 in PCT/JP2021/004277 filed on Feb. 5, 2021 (previously submitted).
Written Opinion of the International Searching Authority dated Apr. 6, 2021, in PCT/JP2021/004277 (with English translation).
International Search Report dated Apr. 6, 2021 in PCT/JP2021/004277 filed on Feb. 5, 2021, 3 pages).

* cited by examiner

SKIN EXTERNAL COMPOSITION

FIELD OF THE INVENTION

The present invention relates to a skin external composition comprising a poorly water-soluble component.

BACKGROUND OF THE INVENTION

Skin external drugs or skin cosmetics contain various physiologically active components or cosmetic components which act on the skin.

A technique to allow drugs or oil components to be supported by nanofibers, which are then applied to the skin, has been reported as one of the approaches for applying various physiologically active components or cosmetic components which act on the skin. For example, Patent Literature 1 discloses a method of allowing oil components to be supported by hollow portions of nanofibers, which are then applied to the skin. Patent Literature 2 discloses a technique of dispersing drugs in nano fibers.
[Patent Literature 1] JP-A-2012-12714
[Patent Literature 2] JP-A-2014-55119

DISCLOSURE OF THE INVENTION

The present invention relates to an assembly of fiber comprising: (a) a polymer soluble in water and an alcohol or a ketone; and (b) a poorly water-soluble component.

The assembly of fiber preferably comprises 50 mass % or more and 98 mass % or less of the component (a) with respect to the whole assembly of fiber.

The assembly of fiber preferably comprises 2 mass % or more and 40 mass % or less of the component (b) with respect to the whole assembly of fiber.

The assembly of fiber is preferably an assembly of fiber for use in production of a liquid skin external composition.

The present invention also relates to a kit comprising the assembly of fiber and an aqueous medium.

The present invention further relates to a method for applying a liquid composition to the skin, comprising the step of dissolving the assembly of fiber in an aqueous medium to obtain the liquid composition.

The present invention further relates to use of the assembly of fiber for production of a liquid skin external composition.

The present invention further relates to a method for producing a liquid skin external composition, the method comprising dissolving the assembly of fiber in an aqueous medium to obtain a liquid composition.

The present invention further relates to a liquid skin external composition comprising: (A) an assembly of fiber formed from a polymer soluble in water and an alcohol or a ketone; (B) a poorly water-soluble component; and (C) an aqueous composition.

The component (C) preferably comprises 60 mass % or more of water.

Liquid droplets comprising the component (B) are preferably dispersed in a liquid comprising the component (C) as the main component.

The liquid skin external composition is preferably a liquid skin external composition in a liquid-liquid dispersion form.

Other features of the present invention will become apparent from the claims and the following description.

DETAILED DESCRIPTION OF THE INVENTION

Figure 1:
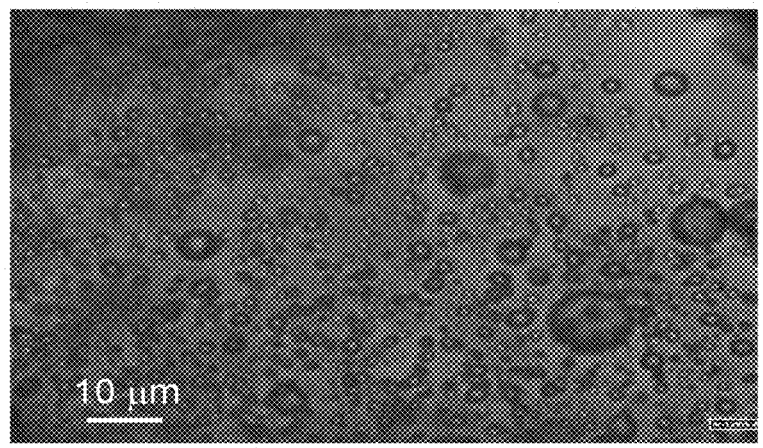
FIG. 1 is an optical microscope image showing that the skin external composition of the present invention is in the form of a liquid-liquid dispersion (Test Example 3).

When the upper limit, the lower limit, or the upper and lower limits of a numerical value are herein specified, the values of the upper limit and the lower limit per se are also included. Every numerical value or numerical range equal to or less than the upper limit or equal to or more than the lower limit or within the range of the upper and lower limits of a numerical value shall be construed as being described, even if not specified.

In the present specification, terms such as "a" and "an" shall be construed as meaning "one or more".

It shall be understood in light of the aforementioned disclosure and the following disclosure in the present specification that various changes or modifications can be made in the present invention. Thus, it should be understood that embodiments which are not specified in the present specification can also be carried out according to the present invention within a technical scope based on the claims.

The contents described in the patent literatures mentioned above are incorporated herein by reference in their entirety.

The present application claims the priority based on Japanese Patent Application No. 2020-020136 filed on Feb. 7, 2020 and Japanese Patent Application No. 2021-015623 filed on Feb. 3, 2021. The contents described in Japanese Patent Application Nos. 2020-020136 and 2021-015623 are incorporated herein by reference in their entirety.

The methods described in Patent Literatures 1 and 2 merely allow drugs or the like to be supported into nanofibers and do not improve the applicability of a poorly water-soluble component to the skin.

Thus, the present invention relates to a skin external composition which immobilizes a poorly water-soluble component with a fine particle size and in an amorphous state, and is excellent in applicability to the skin.

The present inventors have conducted energetic studies to allow a poorly water-soluble component to be stably present in a state with a small particle size in a composition without using a surfactant, and to apply the composition in a liquid state directly to the skin. The present inventors have prepared an assembly of fiber such as a nanofiber deposit or a crushed product thereof by electrospinning using a polymer soluble in water and an alcohol or a ketone, and a poorly water-soluble component, and consequently found that the poorly water-soluble component is immobilized in an amorphous state in the obtained assembly of fiber. Subsequently, the present inventor has mixed the assembly of fiber with an aqueous medium and consequently found that a liquid skin external composition in a liquid-liquid dispersion form is obtained in which liquid droplets containing the poorly water-soluble component are dispersed in a liquid comprising the aqueous medium as the main component.

In the present invention, since the poorly water-soluble component can be immobilized in an amorphous state in a fiber structure, the amorphous state can be maintained over a longer time than the case of having the amorphous state in a liquid. The form of the assembly of fiber is excellent in portability and facilitates to know the amount of usage.

The amorphous state of the poorly water-soluble component in the fiber structure improves solubility upon mixing with an aqueous medium and facilitates to obtain a supersaturated state. This can elevate the dissolution concentration of the poorly water-soluble component dissolved in an aqueous medium. The liquid skin external composition in a liquid-liquid dispersion form thus obtained permits direct contact of the poorly water-soluble component with the skin and can thereby efficiently apply the poorly water-soluble component, i.e., apply a higher concentration of a low water-soluble agent, to the skin.

The present invention provides a skin external composition which immobilizes a poorly water-soluble component with a fine particle size and in an amorphous state, and is excellent in applicability to the skin.

The assembly of fiber of the present invention specifically means a "nanofiber deposit or crushed product thereof".

The assembly of fiber of the present invention contains: (a) a polymer soluble in water and an alcohol or a ketone; and (b) a poorly water-soluble component.

The "water and alcohol or ketone" means "water and alcohol" or "water and ketone".

The assembly of fiber of the present invention is preferably a nanofiber deposit or a crushed product thereof. The nanofiber deposit or the pulverized product thereof includes the deposit itself including a nonwoven fabric formed from nanofibers as well as a processed product such as a compressed or tableted product of the deposit, a cut product, or a compression-molded product of the pulverized product.

The assembly of fiber of the present invention, for example, the nanofiber deposit, can be produced by electrospinning a solution of the component (a) and the component (b) dissolved in a solvent containing an alcohol or a ketone. The crushed product of the nanofiber deposit can be produced by crushing the obtained nanofiber deposit.

The component (a) is a polymer which is soluble in water and soluble in an alcohol or a ketone. Among them, a polymer having the ability to form fibers is preferable.

The polymer soluble in water refers to a polymer having properties by which in an environment of 1 atom and 23° C. where 1 g of the polymer is weighed and then dipped in 10 g of deionized water, 0.5 g or more of the dipped polymer is dissolved in the water after a lapse of 24 hours. The polymer soluble in an alcohol refers to a polymer having properties by which in an environment of 1 atom and 23° C. where 1 g of the polymer is weighed and then dipped in 10 g of ethanol, 0.5 g or more of the dipped polymer is dissolved in the ethanol after a lapse of 24 hours. The polymer soluble in ketone refers to a polymer having properties by which in an environment of 1 atom and 23° C. where 1 g of the polymer is weighed and then dipped in 10 g of acetone, 0.5 g or more of the dipped polymer is dissolved in the acetone after a lapse of 24 hours. In this context, the term "dissolved" means that the polymer, when mixed with water, an alcohol or a ketone, is in a dispersed state in the water, the alcohol or the ketone at 20° C. and this dispersed state is a visibly homogeneous state, preferably a visibly transparent or semitransparent state.

Examples of the component (a) include: natural polymers such as mucopolysaccharides including pullulan, hyaluronic acid, chondroitin sulfate, poly-γ-glutamic acid, modified corn starch, β-glucan, glucooligosaccharide, heparin, and keratosulfate, cellulose, pectin, xylan, lignin, glucomannan, galacturonic acid, psyllium seed gum, tamarind seed gum, gum arabic, tragacanth gum, soybean water-soluble polysaccharide, alginic acid, carrageenan, laminaran, agar (agarose), fucoidan, methylcellulose, hydroxypropylcellulose, and hydroxypropylmethylcellulose; and synthetic polymers such as partially saponified polyvinyl alcohol (in the case of being not used in combination with a cross-linking agent), low saponified polyvinyl alcohol, polyvinylpyrrolidone, methacrylic acid copolymers, polyethylene oxide, and sodium polyacrylate. One or more of these polymers soluble in water and an alcohol can be used alone or in combination. Among these polymers, one or more synthetic polymers selected from the group consisting of a partially saponified polyvinyl alcohol, a low saponified polyvinyl alcohol, polyvinylpyrrolidone and a methacrylic acid copolymer are preferably used, and one or more selected from the group consisting of polyvinylpyrrolidone and a methacrylic acid copolymer are more preferably used, from the viewpoint of easiness in the production of the nanofiber deposit.

The content of the component (a) in the assembly of fiber (specifically, the nanofiber deposit or the crushed product thereof (also simply referred to as "nanofibers")) is preferably 50 mass % or more and 98 mass % or less from the viewpoint of the formability of the nanofiber deposit by electrospinning, from the viewpoint of forming the poorly water-soluble component as amorphous fine particles in the assembly of fiber, and from the viewpoint of dispersing, in a liquid droplet state, the poorly water-soluble component in a dispersion medium mixed with the assembly of fiber.

The content of the component (a) in the assembly of fiber is preferably 55 mass % or more, more preferably 60 mass % or more, further preferably 65 mass % or more, from the viewpoint of the formability of the nanofiber deposit by electrospinning and the amorphous fine particle formability of the poorly water-soluble component.

The content of the component (a) in the assembly of fiber is preferably 96 mass % or less, more preferably 90 mass % or less, from the viewpoint of the amorphous fine particle formability of the poorly water-soluble component.

The component (b) can be a component which is poorly soluble in water and acts on the skin or a human, and is not limited by its function by any means.

The poor water solubility refers to properties by which in an environment of 1 atom and 20° C. where 1 g of the compound is weighed and then dipped in 10 g of deionized water, the amount of the dipped compound dissolved is 0.5 g or less after a lapse of 24 hours.

The amount of the poorly water-soluble component dissolved as mentioned above is preferably 0.0001 g or more, more preferably 0.001 g or more, from the viewpoint of improving the effect of being stably dispersed in an aqueous solvent such as water.

The component (b) is preferably a component having a melting point of 20° C. or higher, more preferably a component having a melting point of 40° C. or higher, from the viewpoint of dispersing a component which is poorly soluble in water, usually precipitates, and is thus difficult to disperse in an aqueous solvent.

The component (a) and the component (b) contained in the assembly of fiber are analyzed as follows.

First, the assembly of fiber is dissolved in water. Then, a component which is poorly soluble in water is separated by filtration. The filtered liquid component is dried to extract a component which is a polymer soluble in water.

Each component thus obtained is subjected to various analyses such as NMR (nuclear magnetic resonance) analysis and IR (infrared spectroscopy) analysis. The structure of a molecular skeleton and the terminal functional group structure of a molecular structure are identified on the basis of signals and spectral positions obtained by each of these analyses. In this way, the types of the contained components are identified.

When each component contains multiple compounds, the structure of a molecular skeleton and the terminal functional group structure of a molecular structure are identified on the basis of signals and spectral positions obtained by each of the analyses, after which the types of the contained components are identified while the amount of each component contained can be calculated from the intensity of measurement values indicating molecular structures corresponding to various components.

The poorly water-soluble compound thus obtained is subjected to DSC analysis. Its melting point can be measured from a melting peak temperature obtained by this analysis.

Examples of the component (b) include polyphenol compounds, amphipathic lipids such as ceramides, lipophilic vitamins, phytosterols, hexylresorcinol, glycyrrhetinic acid and derivatives thereof, salicylic acid and derivatives thereof, steroids and derivatives thereof, monoterpenes and derivatives thereof, and ubiquinone and derivatives thereof. Among them, polyphenol compounds, ceramides, lipophilic vitamins, phytosterols, glycyrrhetinic acid or a derivative thereof, steroids or a derivative thereof, and monoterpenes or a derivative thereof are preferred from the viewpoint of improving the advantageous effects of the present invention. The function of the component (b) is not limited. Examples thereof include antibacterial components, bactericidal components, beauty components such as antioxidative components, whitening components, and anti-wrinkle components, hair growth components, insect and moth repellent components, fragrances, essential oils, amphipathic lipids, odor control components, and skin cooling components.

Examples of the polyphenol as the component (b) include flavonoid compounds as polyphenol compounds. Examples of the flavonoid compounds include flavones, isoflavones, coumarin, chromone, dicumarol, chromanone, chromanol, and their isomers (e.g., cis/trans isomers) and derivatives, ellagic acid, and one or more (or a mixture of two or more thereof) selected from these compounds. Preferred examples of the flavones and the isoflavones include unsubstituted flavones, unsubstituted isoflavones, daidzein (7,4'-dihydroxyisoflavone), genistein (5,7,4'-trihydroxyisoflavone), equol (7,4'-isoflavandiol), apigenin (4',5,7-trihydroxyflavone), quercetin (2-(3,4-dihydroxyphenyl)-3,5,7-trihydroxy-4H-chromen-4-one), 5,7-dihydroxy-4'-methoxyisoflavone, 7,2'-dihydroxyflavone, 3',4'-dihydroxynaphthoflavone, 7,8-benzoflavone, 4'-hydroxyflavone, 5,6-benzoflavone, soybean isoflavone (e.g., isoflavone extracted from soybeans), and such mixtures of other plant, fungal, or bacterial origins (e.g., red clover (*Trifolium pratense*)), and their mixtures.

Other preferred examples of the flavonoid include hesperetin, hesperidin and their mixtures. Other examples of the polyphenol compounds include tetrahydrocurcuminoids. Examples of the tetrahydrocurcuminoids include tetrahydrocurcumin (INCI name: tetrahydrodiferuloylmethane), tetrahydrodemethoxycurcumin (INCI name: tetrahydrodemethoxydiferuloylmethane), and tetrahydrobismethoxycurcumin (INCI name: tetrahydrobisdemethoxydiferuloylmethane).

The chromone and the chromone derivative are preferably compounds having a linear or branched alkyl group having 1 to 15 carbon atoms at position 2 of chromone, i.e., 4H-1-benzopyran-4-one, and having a hydrogen atom, a hydroxy group or an alkoxy group at position 7 thereof.

Examples of such a chromone derivative include 2-butylchromone, 2-pentylchromone, 2-heptylchromone, 2-nonylchromone, 2-hexadecylchromone, 2-(1-ethylpentyl) chromone, 2-butyl-7-methoxychromone, 2-pentyl-7-methoxychromone, 2-heptyl-7-methoxychromone, 2-nonyl-7-methoxychromone, 2-pentadecyl-7-methoxychromone, 2-(1-ethylpentyl)-7-methoxychromone, 7-hydroxy-2-methylchromone, 7-hydroxy-2-butylchromone, 7-hydroxy-2-pentylchromone, 7-hydroxy-2-heptylchromone, 7-hydroxy-2-nonylchromone, 7-hydroxy-2-pentadecylchromone, and 7-hydroxy-2-(1-ethylpentyl)chromone.

Examples of the amphipathic lipids as the component (b) include: higher fatty acids such as myristic acid and stearic acid; higher alcohols such as cetanol, stearyl alcohol, and behenyl alcohol; sphingosines such as sphingosine; and ceramides. The ceramides include, for example, ceramides having various structures called type 1 to type 6 described in Robson K. J. et al., J. Lipid Res., 35, 2060 (1994) and Wertz P. W. et al., J. Lipid Res., 24, 759 (1983), and ceramide-like compounds (e.g., N-(2-hydroxy-3-hexadecyloxypropyl)-N-2-hydroxyethylhexadecanamide) described in JP-A-62-228048. The ceramides have any of sphingosine and phytosphingosine skeletons to which fatty acid, α-hydroxylic acid or ω-hydroxylic acid is bonded through an amide bond. This includes some compounds differing in the number of carbon atoms in fatty acid and the degree of unsaturation. All of these compounds are highly crystalline, also have a high melting point, and are in a solid state at room temperature (20° C.). Among them, (2S,3R)-2-octadecanoylaminooctadecane-1,3-diol (hereinafter, referred to as ceramide 2) and N-2-hydroxystearoylphytosphingosine (hereinafter, referred to as ceramide 6) are preferred because of availability in the market. These compounds may be obtained by extraction from animals or plants or by synthesis, though the obtainment method is not limited thereto. Specific examples thereof include N-stearoylphytosphingosine (manufactured by Nikko Chemicals Co., Ltd.), ceramide HO3 (manufactured by Croda Japan K.K.), ceramide III, ceramide IIIB, ceramide IIIA, ceramide IV, and phytoceramide I (all from Degussa AG), ceramide II (Sederma S.A.), and ceramide TIC-001 (manufactured by Takasago International Corp.). Ceramide is a component constituting stratum corneum intercellular lipids and is therefore known to be effective from the viewpoint of moisturizing properties, barrier functions, etc. for the skin.

Examples of the lipophilic vitamins as the component (b) include vitamin A such as retinol, α-carotene, β-carotene, γ-carotene, and cryptoxanthin, various vitamins D, and tocopherol and derivatives thereof. Examples of the tocopherol and the derivative thereof include tocopherol succinic acid ester, nicotinic acids, vitamins E such as α-tocopherol, dl-α-tocopherol acetate, tocopherol nicotinate, and natural vitamin E.

The phytosterols as the component (b) can be synthetic or naturally derived and can be used as a pure compound or a mixture of compounds (e.g., extracts from a natural resource). The phytosterols are generally found in an unsaponifiable fraction of plant fat/oil and is available as free sterol, an acetylated derivative, sterol ester, or an ethoxylated or glycoside derivative. Typical examples of the phytosterols include β-sitosterol, campesterol, brassicasterol, δ-5-avenasterol, lupeol, α-spinasterol, and stigmasterol.

The hexylresorcinol as the component (b) is known to have properties as a bactericidal agent or a bug repellent and is also known as a therapeutic agent for skin infections or an antioxidant. Examples of the glycyrrhetinic acid or the derivative thereof as the component (b) include β-glycyrrhetinic acid, glycerin glycyrrhetinate, and stearyl glycyrrhetinate. These compounds are known to have an effect as an anti-inflammatory agent. Examples of the salicylic acid or the derivative thereof as the component (b) include salicylic acid, methyl salicylate, and salicylamide. These compounds are known to have an anti-inflammatory, antipyretic, or analgesic effect, etc.

The steroid as the component (b) refers to a hormone having a steroid skeleton, and medicaments supplemented with the steroid are generally called steroid agents. Examples of the steroids include estrogen, progesterone, testosterone, dehydroepiandrosterone, prednisolone, prednisone, progesterone, and pregnenolone.

Examples of the monoterpenes as the component (b) include linalool, menthol, and camphor. Carvacrol, thymol, isopropylmethylphenol, and the like are known as monoterpene derivatives. For example, bactericidal properties, antibacterial properties, and the like are known for the thymol. The bactericidal performance is known for isopropylmethylphenol; blood circulation promotion and anti-inflammatory analgesia are known for the camphor; and psychroesthesia, analgesia, enhancement in anti-inflammatory analgesia, and the like are known for the menthol. In the present invention, thymol, camphor, or menthol in a solid state at 20° C. can be more preferably used.

Examples of the ubiquinone or the derivative thereof as the component (b) include oxidized ubiquinone and ubiquinol which is reduced ubiquinone, also called coenzyme Q, coenzyme Q10, CoQ10, and ubidecarenone.

Examples of the component (b) which is used as an antibacterial component or a bactericidal component include phenol antibacterial agents. Examples of the phenol antibacterial agent include: chlorophenol antibacterial agents such as triclosan, chlorothymol, carvacrol, chlorophene, dichlorophene, hexachlorophene, chloroxylenol, and chlorocresol; and O-phenylphenol, isopropylmethylphenol, and thymol. Among them, isopropylmethylphenol and thymol are more preferred.

Examples of the hair growth component include: flavanol derivatives such as trans-3,4'-dimethyl-3-hydroxyflavanone; nicotinic acids such as benzyl nicotinate, tocopherol nicotinate, and β-butoxyethyl nicotinate; vitamins E such as α-tocopherol, dl-α-tocopherol acetate, tocopherol nicotinate, and natural vitamin E; and minoxidil, bimatoprost, tafluprost, nonanoic acid vanillylamide, and St. John's wort (*Hypericum erectum*) extracts.

The content of the component (b) in the assembly of fiber is preferably 2 mass % or more and 40 mass % or less from the viewpoint of the formability of the nanofiber deposit by electrospinning, from the viewpoint of the amorphous fine particle formability of the poorly water-soluble component into the nanofiber deposit, and from the viewpoint of dispersing a liquid of the poorly water-soluble component in an aqueous medium when the aqueous medium is mixed with the assembly of fiber.

The content of the component (b) in the assembly of fiber is preferably 3 mass % or more, more preferably 5 mass % or more, further preferably 8 mass % or more, from the viewpoint of the amorphous fine particle formability of the nanofiber deposit by electrospinning, improvement in the dispersibility of the poorly water-soluble component, and the applicability of a higher concentration of the poorly water-soluble component to a subject.

The content of the component (b) in the assembly of fiber is preferably 40 mass % or less, more preferably 35 mass % or less, further preferably 30 mass % or less, from the viewpoint of the amorphous fine particle formability of the poorly water-soluble component and being able to maintain the amorphous state of the poorly water-soluble component even when the assembly of fiber is stored for a long time.

The content of the component (b) in the assembly of fiber is particularly preferably 20 mass % or less from the viewpoint of stability after mixing with an aqueous medium.

The mass ratio of the component (a) to the component (b) (mass of the component (a)/mass of the component (b)) in the assembly of fiber is preferably 2 or more, more preferably 2 or more and 49 or less, from the viewpoint of the amorphous fine particle formation of the poorly water-soluble component into the assembly of fiber, from the viewpoint of dispersing a liquid of the poorly water-soluble component in an aqueous medium when the aqueous medium is mixed with the assembly of fiber, and from the viewpoint of maintaining the amorphous state of the poorly water-soluble component in the assembly of fiber.

The mass ratio is preferably 2 or more, more preferably 3 or more, further preferably 4 or more, from the viewpoint of facilitating maintaining the amorphous state of the poorly water-soluble functional component in the assembly of fiber.

The mass ratio is preferably 19 or less, more preferably 11 or less, from the viewpoint of permitting application of a higher concentration of the poorly water-soluble functional component to the skin.

The assembly of fiber can be produced by electrospinning a solution of the component (a) and the component (b) dissolved therein. The solvent of the solution containing the component (a) and the component (b) for use in electrospinning is preferably one or more volatile solvents selected from the group consisting of an alcohol and a ketone. The solvent may contain water.

In the electrospinning method, the component (a) and the component (b) are discharged from a nozzle tip onto a base material or a human skin after sufficient charging of the solution containing the component (a) and the component (b) placed in the electric field. As the solution containing the component (a) and the component (b) is evaporated, the charge density of the solution becomes excessive, so that the solution containing the component (a) and the component (b) is further evaporated while refined by Coulomb repulsion, eventually forming a dry assembly of fiber.

For example, a monohydric chain aliphatic alcohol, a monohydric cyclic aliphatic alcohol, or a monohydric aromatic alcohol is preferably used as the solvent alcohol. Examples of the monohydric chain aliphatic alcohol include linear or branched alcohols having 1 to 6 carbon atoms. Examples of the monohydric cyclic aliphatic alcohol include cyclic aliphatic alcohols having 4 to 6 carbon atoms. Examples of the monohydric aromatic alcohol include benzyl alcohol and phenylethyl alcohol. Specific examples thereof include methanol, ethanol, isopropyl alcohol, n-propyl alcohol, n-butyl alcohol, 2-butyl alcohol, isobutyl alcohol, 2-methyl-2-propyl alcohol, n-pentanol, 2-pentanol, 3-pentanol, 2-methyl-1-butyl alcohol, 2-methyl-2-butyl alcohol, 3-methyl-1-butyl alcohol, 3-methyl-2-butyl alcohol, neopentyl alcohol, n-hexanol, 2-hexanol, 3-hexanol, 2-methyl-1-pentanol, 3-methyl-1-pentanol, 4-methyl-1-pentanol, 2-methyl-2-pentanol, 3-methyl-2-pentanol, 4-methyl-2-pentanol, 2-methyl-3-pentanol, 3-methyl-3-pentanol, 2,2-dimethyl-1-butanol, 2,3-dimethyl-1-butanol, 3,3-dimethyl-1-butanol, 2,3-dimethyl-2-butanol, 3,3-dimethyl-2-butanol, 2-ethyl-1-butanol, cyclobutanol, cyclopentanol, cyclohexanol, benzyl alcohol, and phenylethyl alcohol. One or more selected from the group consisting of these alcohols can be used alone or in combination of two or more.

Examples of the solvent ketone include acetone, diethyl ketone, methyl propyl ketone, methyl amyl ketone, methyl ethyl ketone, methyl isobutyl ketone, methyl-n-hexyl ketone, methyl-n-propyl ketone, diisopropyl ketone, diisobutyl ketone, and hexafluoroacetone. These ketones can be used alone or in combination of two or more.

The solvent is preferably one or more selected from the group consisting of an alcohol and a ketone, more preferably one or two selected from the group consisting of an aliphatic alcohol having 1 to 6 carbon atoms and an aliphatic ketone having 1 to 6 carbon atoms. The solvent is more preferably one or more selected from the group consisting of ethanol, isopropyl alcohol, n-butyl alcohol and acetone, further preferably one or more selected from the group consisting of ethanol, isopropyl alcohol and acetone, even more preferably ethanol.

In a more preferred form, the content of the solvent (preferably an alcohol or a ketone) in the solution containing the component (a) and the component (b) is preferably 50 mass % or more and 94 mass % or less, more preferably 50 mass % or more and 92 mass % or less, further preferably 50 mass % or more and 90 mass % or less, from the viewpoint of the formability of the assembly of fiber of interest.

The solvent may contain water. The content of the water is preferably 5 mass % or less, more preferably 1 mass % or less, in the solvent from the viewpoint of the stability of the poorly water-soluble component in the assembly of fiber or composition, and is preferably 0.1 mass % or more from the viewpoint of electrospinnability.

The content of the component (a) is preferably 5 mass % or more and 40 mass % or less, more preferably 6 mass % or more and 35 mass % or less, further preferably 8 mass % or more and 30 mass % or less, in the solution from the viewpoint of the formability of the assembly of fiber of interest.

The content of the component (b) is preferably 0.05 mass % or more and 20 mass % or less, more preferably 0.5 mass % or more and 15 mass % or less, further preferably 1 mass % or more and 10 mass % or less, in the solution from the viewpoint of the formability of the assembly of fiber of interest.

The total content of the component (a) and the component (b) in the solution is preferably 5.05 mass % or more and 50 mass % or less, more preferably 6.05 mass % or more and 45 mass % or less, further preferably 6.05 mass % or more and 40 mass % or less, even more preferably 9 mass % or more and 35 mass % or less, further preferably 9 mass % or more and 32 mass % or less, from the viewpoint of efficiently and stably forming the assembly of fiber.

The solution may contain, in addition to the component (a) and the component (b), an additive such as a plasticizer, a sensory enhancer, a conductivity regulator, a color pigment, an extender pigment, a dye, a fragrance, a repellant, an antioxidant, a stabilizer, an antiseptic, or various vitamins unless the additives interfere with the advantageous effects of the present invention.

The plasticizer can impart flexibility to the assembly of fiber formed by electrospinning. Such a plasticizer is preferably an oil agent in a liquid state at 20° C.

The sensory enhancer, when used in combination with the plasticizer, imparts flexibility to the assembly of fiber formed by electrospinning while improving texture (smoothness, oily feeling, friction feeling, stickiness, etc.).

The plasticizer and the sensory enhancer are not particularly limited as long as the plasticizer and the sensory enhancer may generally be used in the cosmetic field. For example, one or more selected from the group consisting of polyols, polyoxyalkylene glycols, polyoxyalkylene alkyl ethers, ester oils, silicone oils, hydrocarbon oils, liquid fats/oils, solid fats/oils, a higher alcohols, and nonionic surfactants can be used alone or in combination.

The conductivity regulator is preferably alkali metal salts or ammonium salts, more preferably ionic surfactants, further preferably one or more selected from the group consisting of cationic surfactants and anionic surfactants, from the viewpoint of conductivity improving properties.

The content of the surfactant in the solution for use in electrospinning, and the content of the surfactant in the component (a) are preferably 0 mass % or more and 50 mass % or less, more preferably 25 mass % or less, with respect to the amount of the poorly water-soluble component in the assembly of fiber from the viewpoint of improving applicability to the skin.

Such an additive and a surfactant component in the solution for use in electrospinning can be identified by the following approach: the assembly of fiber to be measured is dissolved in various solvents, and the solutions are analyzed by pyrolysis gas chromatography (GC-MS). Compounds are identified from the mass spectra thus obtained, while their contents are calculated.

The range of the viscosity of the solution for use in electrospinning containing the component (a) and the component (b) is preferably 2 mPa·s or more and 3 000 mPa·s or less, more preferably 5 mPa·s or more and 2 000 mPa·s or less, further preferably 10 mPa·s or more and 1 500 mPa·s or less, even more preferably 30 mPa·s or more and 1 000 mPa·s or less, further preferably 50 mPa·s or more and 800 mPa·s or less, even further preferably 80 mPa·s or more and 500 mPa·s or less.

The viscosity of the solution is measured at 25° C. using a type B viscometer. Type B viscometer (TVB-10M) manufactured by Toki Sangyo Co., Ltd. can be used as the type B viscometer. In this case, measurement conditions involve a measurement temperature of 25° C. In this respect, the measurement temperature is the temperature of the solution. The type of a rotor and the number of rotor rotations are selected in accordance with the viscosity of the solution and in accordance with the specifications of the measurement equipment used. In the case of using the TVB-10M, the measurement can be performed using a M2 rotor at 6 rpm for a viscosity of a composition for coating formation of 2 500 mPa·s or more, using a M2 rotor at 12 rpm for this viscosity of 1 000 mPa·s or more and less than 2 500 mPa·s, using a M2 rotor at 30 rpm for this viscosity of 500 mPa·s or more and less than 1 000 mPa·s, using a M2 rotor at 60 rpm for this viscosity of 100 mPa·s or more and less than 500 mPa·s, and using a M1 rotor at 60 rpm for this viscosity of less than 100 mPa·s. The specification manual of the TVB-10M states measurement conditions other than the measurement conditions described above, and this viscometer can measure the viscosity under other measurement conditions in accordance with the viscosity of the solution.

Figure 2:
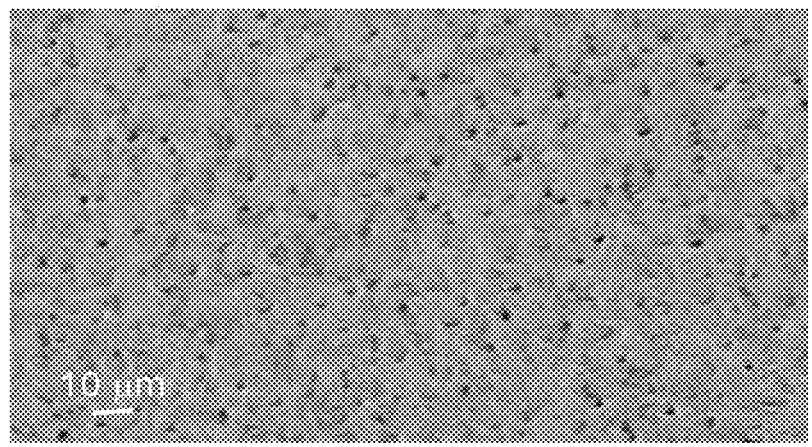
FIG. 2 is an optical microscope image showing that the skin external composition of the present invention is in the form of a liquid-liquid dispersion (Test Example 5).

For the production of the nanofiber deposit by electrospinning using the solution, the solution can be electrospun onto a base material or a human skin using an electrospinning apparatus having a structure described in, for example, FIG. 2 of Patent Literature 1.

The crushed product of the nanofiber deposit can be obtained by crushing the obtained deposit.

The resulting assembly of fiber contains the component (a) and the component (b) because the solvent is evaporated by electrospinning.

The resulting assembly of fiber preferably contains 50 mass % or more and 98 mass % or less of the component (a) with respect to the whole assembly of fiber, and 2 mass % or more and 40 mass % or less of the component (b) with respect to the whole assembly of fiber.

The average fiber diameter of the assembly of fiber is preferably 20 nm or larger, more preferably 30 nm or larger, further preferably 50 nm or larger, from the viewpoint that enhanced strength of nanofibers facilitates maintaining a fiber form and therefore prevents the poorly water-soluble functional component dispersed in nanofibers from being deformed and facilitates maintaining the amorphous state thereof, while increase in particle size by aggregation can be suppressed.

The average fiber diameter is preferably 5 000 nm or smaller, more preferably 4 000 nm or smaller, further preferably 3 000 nm or smaller, from the viewpoint of facilitating rapidly dissolving the assembly of fiber, and facilitating dispersing liquid droplets of the poorly water-soluble component in a dispersion medium.

The fiber diameter is the cross-sectional diameter of a fiber, as a rule. In this context, the fiber diameter is the diameter when the cross section of the fiber is a circle, and is a major axis when the cross section is an ellipse. The fiber diameter can be measured, for example, by observing fibers by scanning electron microscopic observation at a magnification of 2 000× or 5 000×, arbitrarily selecting 100 fibers except for defects (e.g., clumps of fibers and crossing portions of fibers) from the two-dimensional image, drawing lines orthogonal to the longitudinal directions of the fibers, and directly reading their fiber diameters. As for the average fiber diameter, an arithmetic average of these measurement values is determined and regarded as the average fiber diameter.

The CV value of the average fiber diameter of the nanofiber deposit is preferably from 10 to 100%, more preferably from 12 to 95%, further preferably from 15 to 90%, from the viewpoint of forming a network by nanofibers in the deposit.

The fiber diameter of the crushed product of the nanofiber deposit is the same as that of the assembly of fiber.

The average fiber length of the crushed product is preferably 20 μm or larger and 300 μm or smaller, more preferably 30 μm or larger and 250 μm or smaller, further preferably 40 μm or larger and 200 μm or smaller. The fiber length can be measured, for example, by observing fibers by scanning electron microscopic observation at a magnification of from 250× to 750× in accordance with the lengths of the fibers, arbitrarily selecting 100 fibers except for defects (e.g., clumps of fibers and crossing portions of fibers) from the two-dimensional image, drawing lines orthogonal to the longitudinal directions of the fibers, and directly reading their fiber lengths. As for the average fiber length, an arithmetic average of these measurement values is determined and regarded as the average fiber length.

The CV value of the average fiber length of the crushed product of the nanofiber deposit is preferably from 40 to 100%, more preferably from 42 to 95%, further preferably from 45 to 90%, from the viewpoint of forming a network when the crushed product of the nanofiber deposit is applied onto the skin, and from the viewpoint of applicability to the skin. Whether or not fibers in the nanofiber deposit form a network can be confirmed under a scanning electron microscope or the like. The network is a state in which fibers dispersed in the nanofiber deposit have intersection points with each other at two or more locations and thereby have space between the fibers.

In the present invention, whether or not the poorly water-soluble component in the assembly of fiber is present in an amorphous state can be confirmed from the presence or absence of a detection peak obtained by X-ray diffraction (XRD) analysis. Specifically, when the poorly water-soluble component is present as a crystal, a detection peak derived from the crystal structure of the poorly water-soluble component is confirmed by X-ray diffraction analysis. In contrast, when the poorly water-soluble component is present in an amorphous state, the peak derived from the crystal structure is not confirmed. Fine particles of the poorly water-soluble component can be confirmed by the measurement of a relaxation time by solid NMR.

Specifically, longitudinal relaxation (spin-lattice relaxation) time T1, and longitudinal relaxation time T1ρ in the rotational system are measured in solid NMR measurement. Effective spin diffusion length L is obtained in accordance with the following equation using these relaxation times (T1 and T1ρ) and spin diffusion coefficient D of an organic solid, and the effective spin diffusion length L thus obtained is regarded as information on the distance between organic materials, i.e., a particle size.

$$L=(6 \times D \times t)^{(1/2)}$$

Measurement conditions of the solid NMR involve cutting the assembly of fiber into approximately 5 mm, and packing a ϕ7 mm sample tube therewith. Then, $^{13}$C-CPMAS spectra are measured using Bruker DSX300WB and a 7 mm MAS probe. The signal positions of a polymer constituting the fibers, and the poorly water-soluble functional component are identified from the $^{13}$C-CPMAS spectra. The relaxation times T1 and T1ρ are measured at these signal positions. In this respect, when the polymer and the poorly water-soluble functional component have substantially the same T1 or T1ρ, the particle size is regarded as being smaller than the L value calculated in accordance with the equation on the premise that the relaxation times of the polymer and the poorly water-soluble functional component agree with each other by spin diffusion. When the polymer and the poorly water-soluble functional component have different T1 or T1ρ, the particle size can be regarded as being larger than the L value calculated in accordance with the equation. The particle size is identified from these calculation results.

In the present invention, it can be considered that the poorly water-soluble component is dispersed as fine particles in the assembly of fiber and can thereby be stored in an amorphous state for a long time.

The poorly water-soluble component in an amorphous state having a smaller particle size is more difficult to crystallize over time. Therefore, a small particle size of the component (b) contained in the fibers is preferred. Specifically, the particle size is preferably 10 nm or smaller, more preferably 5 nm or smaller, further preferably 3 nm or smaller.

Realistically, the particle size is 0.1 nm or larger.

In the present invention, the assembly of fiber containing the component (a) and the component (b) can be mixed with an aqueous medium to obtain a liquid skin external composition containing: (A) an assembly of fiber formed from a polymer soluble in water and an alcohol or a ketone; (B) a poorly water-soluble component; and (C) an aqueous medium.

The composition can be a liquid skin external composition in a liquid-liquid dispersion form in which liquid droplets containing the component (B) are dispersed in an amorphous state in a liquid comprising the component (C) as the main component; the component (A) is dissolved in the component (C); and the component (B) is dissolved in a supersaturated state. Particularly, the best supersaturated state is obtained immediately after mixing of the assembly of fiber with the aqueous medium.

In this context, the supersaturated state means that, when solubility is defined as the concentration of the component (B) after a lapse of a sufficient time from the dissolution of the component (B) in the component (C) in an environment of 20° C. and 50%, the component (B) is dissolved at a level equal to or more than the solubility in the component (C).

In order to confirm the supersaturated state of the component (B), first, the assembly of fiber containing the component (a) and the component (b) is mixed with the aqueous medium in an environment of 20° C. and 50%, and then, the mixture is filtered through a membrane filter having an opening of 0.2 µm to obtain a filtrate. Then, the obtained filtrate is left to stand for 24 hours or longer in the same environment. When a precipitate of the component (B) emerges in the filtrate thus left to stand for 24 hours, it can be said that the component (B) is dissolved in a supersaturated state in the component (C).

In order to obtain the liquid skin external composition in a liquid-liquid dispersion form in which amorphous liquid droplets containing the component (B) are dispersed in a liquid comprising the component (C) as the main component; the component (A) is dissolved in the component (C); and the component (B) is dissolved in a supersaturated state, it is preferred to mix the assembly of fiber containing the component (a) and the component (b) with an aqueous medium containing 60 mass % or more of water.

In this context, examples of the assembly of fiber containing the component (a) and the component (b) include the assembly of fiber mentioned above. Preferred contents of the component (a) and the component (b) are also as mentioned above.

The liquid-liquid dispersion formed by the liquid skin external composition obtained according to the present invention can be confirmed by placing the assembly of fiber on a glass slide, placing a glass cover thereon, applying the aqueous medium containing 60 mass % or more of water from the gap between the glass slide and the glass cover, and observing a liquid of the assembly of fiber dissolved therein under an optical microscope.

The component of the liquid droplets constituting the liquid-liquid dispersion can be determined by conducting microscopic FT-IR analysis, determining a molecular structure from IR spectra obtained from liquid droplet surface, and identifying the composition of the component contained therein.

The amorphous state of the liquid droplets of the component (B) in the liquid skin external composition obtained according to the present invention can be confirmed by placing the assembly of fiber on a glass slide, placing a glass cover thereon, applying the aqueous medium containing 60 mass % or more of water from the gap between the glass slide and the glass cover, and observing a liquid of the assembly of fiber dissolved therein under a polarizing microscope to confirm change in color or brightness derived from a crystal structure.

The liquid state of the liquid skin external composition of the present invention refers to a liquid state at 20° C.

Thus, the present invention provides a kit for production of a liquid skin external composition comprising the assembly of fiber containing the component (a) and the component (b), and an aqueous medium as the component (C).

The content of water in the component (C) is preferably 60 mass % or more and 100 mass % or less, more preferably 70 mass % or more and 100 mass % or less, further preferably 80 mass % or more and 100 mass % or less, from the viewpoint of forming the liquid skin external composition in a liquid-liquid dispersion form.

The content of water in the component (C) can be measured by use of a Karl Fischer's method (JIS K 0068).

The component (C) may contain an alcohol having 3 or more carbon atoms in a liquid state at 20° C. when mixed with water at the ratio described above. Such an alcohol is preferably an aliphatic alcohol or a polyhydric alcohol, having 3 to 6 carbon atoms. The alcohol is more preferably one or more selected from the group consisting of: isopropyl alcohol and n-butyl alcohol; alkylene glycols such as ethylene glycol, propylene glycol (PG), 1,3-propanediol, and 1,3-butanediol; polyalkylene glycols such as diethylene glycol, dipropylene glycol (DPG), polyethylene glycol having a weight-average molecular weight of 2 000 or lower, and polypropylene glycol; and glycerins such as glycerin, diglycerin, and triglycerin, further preferably one or more selected from the group consisting of isopropyl alcohol, dipropylene glycol (DPG), propylene glycol (PG) and glycerin, even more preferably dipropylene glycol (DPG).

The total content of an alcohol having 2 or less carbon atoms and a ketone in the component (C) is preferably 40 mass % or less, more preferably 30 mass % or less, further preferably 20 mass % or less, from the viewpoint of the stability of the poorly water-soluble component during or after formation of the liquid skin external composition after application of the component (C), and applicability to the skin.

From a similar viewpoint, for the component (C), the content of an alcohol or a ketone used in an electrospinning liquid constituting the assembly of fiber is preferably 30 mass % or less, preferably 20 mass % or less, even more preferably 10 mass % or less.

The content of a surfactant in the component (C) is preferably 0 mass % or more and 5 mass % or less, more preferably 0 mass % or more and 3 mass % or less, further preferably 0 mass % or more and 1 mass % or less, from the viewpoint of the applicability to the skin of the poorly water-soluble component after formation of the liquid skin external composition. The component (C) may contain substantially no surfactant. The component (C) preferably contains no surfactant from the viewpoint of permitting application of very small liquid droplets in an amorphous state of the poorly water-soluble component to the skin without impairing the barrier function of the skin.

The content of the surfactant in the formed liquid skin external composition is preferably 0 mass % or more and 3 mass % or less, more preferably 0 mass % or more and 1 mass % or less, further preferably 0 mass % or more and 0.5 mass % or less, from the viewpoint of the applicability of the poorly water-soluble component to the skin.

These components in the component (C) may be analyzed by conducting pyrolysis gas chromatography (GC-MS) analysis, and identifying compounds from the mass spectra thus obtained, while calculating their contents from the detection intensity of the mass spectra.

The assembly of fiber can be produced on a base material and be in the form of a sheet. The base material is preferably insoluble in water. In the present invention, the water insolubility of the base material refers to properties by which in an environment of 1 atom and 23° C. where 1 g of the base material is weighed and then dipped in 10 g of deionized water, more than 0.5 g, preferably more than 0.8 g, of the dipped base material is not dissolved after a lapse of 24 hours. In other words, the water insolubility refers to properties by which in an environment of 1 atom and 23° C. where 1 g of the base material is weighed and then dipped in 10 g of deionized water, less than 0.5 g, preferably less than 0.2 g, of the dipped base material is dissolved after a lapse of 24 hours. From this viewpoint, the base material is preferably constituted by a water-insoluble polymer compound. The form of the base material is preferably any of various nonwoven fabrics, meshes, and films.

The thickness of the base material is preferably 3 μm or more, more preferably 5 μm or more, further preferably 10 μm or more. The thickness of the base material is preferably 1 000 μm or less, more preferably 500 μm or less, further preferably 450 μm or less. Specifically, the thickness of the base material is preferably 3 μm or more and 1 000 μm or less, more preferably 5 μm or more and 500 μm or less, further preferably 10 μm or more and 450 μm or less. In this case, the kit has a sheet composition made of the assembly of fiber, and the aqueous medium.

Such a kit having a sheet composition and the aqueous medium is excellent in portability, facilitates knowing the amount of usage, and can secure the stability of the poorly water-soluble component.

The assembly of fiber can be added to the aqueous medium to obtain a liquid composition, and the liquid composition can be applied to the skin. Specifically, the liquid composition may be applied to the skin in 0 minute or longer and 180 minutes or shorter, preferably 0 minute or longer and 30 minutes or shorter, more preferably 0 minute or longer and 10 minutes or shorter, further preferably 0 minute or longer and 5 minutes or shorter, from addition of the assembly of fiber to the aqueous medium. More specifically, the mixing of the assembly of fiber with the aqueous medium may be performed in a container immediately before application to the skin, or may be performed on the skin to which the liquid composition is to be applied.

The liquid composition thus obtained can be applied to the skin within this time range and thereby applied to the skin without excessive aggregation of the liquid droplets containing the poorly water-soluble component and with the poorly water-soluble component being in an amorphous state.

Alternatively, the aqueous medium may be applied to skin surface, and the assembly of fiber can be applied thereonto, so that the assembly of fiber is dissolved in the aqueous medium to form a liquid composition on the skin. Specifically, it is preferred that the assembly of fiber should be prepared in the form of a sheet and its mixing with the aqueous medium should be performed on the skin to which the liquid composition is to be applied, from the viewpoint of applying the liquid droplets containing the poorly water-soluble component directly to the skin.

In the liquid composition, the ratio between the assembly of fiber and the aqueous medium used in combination is preferably 0.0001 mg/mg or more, more preferably 0.001 mg/mg or more, further preferably 0.005 mg/mg or more, in terms of the ratio of the weight (mg) of the assembly of fiber to the weight (mg) of the aqueous medium (mass (mg) of the assembly of fiber/mass (mg) of the aqueous medium), from the viewpoint of facilitating dissolving the poorly water-soluble component in a supersaturated state in the aqueous medium.

From a similar viewpoint, the liquid composition contains preferably 6 mass % or more, more preferably 8 mass % or more, further preferably 10 mass % or more, of water with respect to the whole composition.

In the liquid composition, the ratio of mass (mg) of the assembly of fiber/mass (mg) of the aqueous medium is preferably 10 mg/mg or less, more preferably 9 mg/mg or less, further preferably 8 mg/mg or less, from the viewpoint of the ability of reliably dissolving the assembly of fiber in the aqueous medium and of dispersing the liquid droplets of the poorly water-soluble component.

From a similar viewpoint, the liquid composition contains preferably 99.9 mass % or less, more preferably 99 mass % or less, further preferably 98 mass % or less, of water with respect to the whole composition.

In the case of mixing the assembly of fiber with the aqueous medium in a container, the container can be shaken with a hand after addition of these components to the container. In the case of mixing the components on the skin, the components may be placed on the skin and then rapidly mixed with a finger.

The procedure described above can readily form a liquid skin external composition in a liquid-liquid dispersion form in which liquid droplets containing the component (B) are dispersed in a liquid comprising the component (C) as the main component. In this context, the average particle size of the liquid droplets containing the component (B) is preferably 100 μm or smaller, more preferably 80 μm or smaller, further preferably 50 μm or smaller, from the viewpoint of securing the applicability of the component (B) to the skin.

The average particle size of the liquid droplets according to the present invention is preferably an average particle size within 30 seconds after formation of the liquid skin external composition (after application of the aqueous medium) and is preferably 0.001 μm or larger. The average particle size of the liquid droplets can be measured by placing the assembly of fiber on a glass slide, placing a glass cover thereon, applying the aqueous medium containing 60 mass % or more of water from the gap between the glass slide and the glass cover, observing the liquid droplets at a magnification of from 50× to 1 000× in accordance with the sizes of the liquid droplets under an optical microscope within 30 seconds after the application of the aqueous medium to take an image, arbitrarily selecting 50 liquid droplets from the two-dimensional image, drawing lines in the longitudinal directions of the liquid droplets, and directly reading their fiber lengths. As for the average particle length, an arithmetic average of these measurement values is determined and regarded as the average particle size.

The combination of the component (B) and the component (C) to enable forming of the liquid droplets of the component (B) can be determined from the logarithm of water dissolution concentration S, log S, estimated using commercially available Hansen solubility parameter estimation software HSPiP. When the solubility of the component (B) in water is log S>−5, it can be confirmed by optical microscopic observation that the liquid droplets containing the component (B) can be formed even if the component (C) is water alone. On the other hand, when the solubility of the component (B) in water is log S≤−5, it can be confirmed by optical microscopic observation that the liquid droplets containing the component (B) can be formed by adding a solvent having affinity for the component (B) into the component (C).

Provided that the liquid skin external composition of the present invention is applied to the skin, the poorly water-soluble component can be applied in a liquid form to the skin. Therefore, the poorly water-soluble component can be directly brought into contact with the skin and can be effectively applied to the skin. The direct contact of the poorly water-soluble component with the skin probably improves permeability to the skin or allows the skin to contact with a high concentration thereof, for example. The direct contact according to the present invention is considered as a state in which unlike emulsified particles or the like, the poorly water-soluble component is neither present in micelle nor encapsulated, and preferably, few oil components or surfactants are present between the poorly water-soluble component and the aqueous medium. Use of the kit of the present invention is excellent in portability, facilitates knowing the amount of usage, and can secure the stability of the poorly water-soluble component.

EXAMPLES

Hereinafter, the present invention will be described in more detail with reference to Examples. However, the scope of the present invention is not limited by these Examples. The term "%" means "mass %" unless otherwise specified.

Examples 1 to 4

(Production of Nanofiber Deposit or Crushed Product Thereof)

The component (a) and the component (b) were dissolved in the quantities described in Table 1 in ethanol to obtain a solution having the mass % described in Table 1. In any of these examples, no surfactant was used. This solution was used to form a nanofiber deposit on the surface of a base material with an apparatus of the electrospinning method described in FIG. 2 of Patent Literature 1. Conditions for the production of the nanofiber deposit were as follows.

Since a homogenous solution is instantly dried and immobilized by electrospinning, the solid content ratios (mass %) of the component (a) and the component (b) in the liquid composition shown in Table 1 can be regarded as being the same as the contents (mass) of the components in the obtained assembly of fiber.

Applied voltage: 32 kV
Capillary-collector distance: 160 mm
Amount of aqueous solution discharged: 1 mL/h
Environment: 25° C., 30% RH The nonwoven fabric used as the base material was "Bemliese® SE103", a nonwoven fabric manufactured by Asahi Kasei Corp.

The crushed product was obtained by pulverizing the nanofiber deposit for 5 minutes using a commercially available cutter mill.

(X-Ray Diffraction Evaluation of Assembly of Fiber)

Table 1 shows results of conducting X-ray diffraction evaluation. For this evaluation, measurement was performed under the following conditions using a powder X-ray diffraction apparatus (manufactured by Rigaku Corp., MiniFlex600).

Preparation of measurement sample: a measurement cell was packed with the crushed product of the nanofiber deposit, and pressure was applied thereto to prepare 320 $mm^2$ in area×1 mm thick smooth pellets.

X-ray diffraction analysis conditions: step angle: 0.01°, scan speed: 10°/min, measurement range: diffraction angle 2θ=5 to 40°, X-ray source: Cu/Kα-radiation, tube voltage: 15 kV, tube current: 30 mA This evaluation was also carried out on the poorly water-soluble component contained in nanofibers to determine a diffraction angle at which a crystal peak derived from crystals of the poorly water-soluble component appeared.

When the measurement peak derived from crystals of the contained poorly water-soluble component did not appear in the evaluation of the nanofiber deposit, the poorly water-soluble component was determined as being contained in an amorphous state.

(Solid NMR Evaluation of Assembly of Fiber)

The nanofiber deposit of Example 2 was subjected to the solid NMR evaluation mentioned above.

Here, diffusion coefficient D of spin diffusion of an organic solid was set to $10^{\wedge}(-12)$ $cm^2/s$.

As a result, relaxation times T1ρ obtained from a polymer constituting the fibers, and the poorly water-soluble functional component were calculated as 9.3 ms and 10.1 ms, respectively. Thus, the poorly water-soluble functional component had a particle size of estimated 3 nm or smaller.

TABLE 1

| | Example 1 | | | Example 2 | | | Example 3 | | | Example 4 | | |
|---|---|---|---|---|---|---|---|---|---|---|---|---|
| | Component (a): polymer soluble in water and alcohol or ketone and capable of forming fibers | | | | | | | | | | | |
| | Polyvinylpyrrolidone (*1) | | | Polyvinylpyrrolidone (*1) | | | Polyvinylpyrrolidone (*1) | | | Polyvinylpyrrolidone (*1) | | |
| | Component (b): poorly water-soluble functional component | | | | | | | | | | | |
| | MA293(*3) | | | t-Flavanone | | | Testosterone | | | Ceramide (*4) | | |
| | Mass (g) | Solution ratio (mass %) | Solid content ratio (mass %) | Mass (g) | Solution ratio (mass %) | Solid content ratio (mass %) | Mass (g) | Solution ratio (mass %) | Solid content ratio (mass %) | Mass (g) | Solution ratio (mass %) | Solid content ratio (mass %) |
| Quantity of component (a) | 0.9 | 13.00 | 90.00 | 0.7 | 13.00 | 70.00 | 0.8 | 11.00 | 80.00 | 0.9 | 12.00 | 90.00 |
| Quantity of component (b) | 0.1 | 1.00 | 10.00 | 0.3 | 6.00 | 30.00 | 0.2 | 3.00 | 20.00 | 0.1 | 1.00 | 10.00 |
| Ethanol (*2) | 5.9 | 86.00 | — | 4.4 | 81.00 | — | 6 | 86.00 | — | 6.5 | 87.00 | — |
| Total | 6.9 | 100.00 | 100.00 | 5.4 | 100.00 | 100.00 | 7 | 100.00 | 100.00 | 7.5 | 100.00 | 100.00 |
| X-ray diffraction evaluation of assembly of fiber | Containing component (b) in amorphous state | | | Containing component (b) in amorphous state | | | Containing component (b) in amorphous state | | | Containing component (b) in amorphous state | | |
| Mass of component (a)/ mass of component (b) in assembly of fiber | 9.0 | | | 2.3 | | | 4.0 | | | 9.0 | | |

% means mass %
*1 PVP Luviskol K90 (manufactured by BASF SE)
*2 Ethanol (99.5) Wako Grade 1 (FUJIFILM Wako Pure Chemical Corp.)
*3 2-(1-Ethylpentyl)-7-methoxychromone
*4 N-(2-Hydroxy-3-hexadecyloxypropyl)-N-2-hydroxyethylhexadacanamide Test Examples 1 to 13

Each of the nanofiber deposits of Examples 1 to 4 was placed on a glass slide. A glass cover was placed thereon. The aqueous medium (c) of Table 2 was applied from the gap between the glass slide and the glass cover. An image was taken under an optical microscope within 30 seconds after the application of the aqueous medium. Liquid droplets, if any, were observed at a magnification of from 50× to 1 000× in accordance with the sizes of the liquid droplets to take an image. An average particle size was determined.

The Hansen solubility of the poorly water-soluble component (b) and the aqueous medium (c) was estimated using commercially available Hansen solubility parameter estimation software HSPiP.

The fiber thicknesses of the nanofibers in the nanofiber deposit were determined by scanning electron microscopic (SEM) observation.

(Microscopic Observation)

Figure 3:
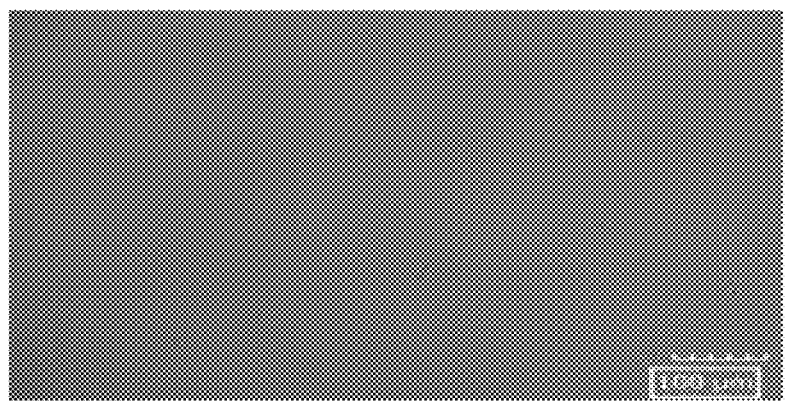
FIG. 3 is an optical microscope image of Test Example 1.
Figure 4:
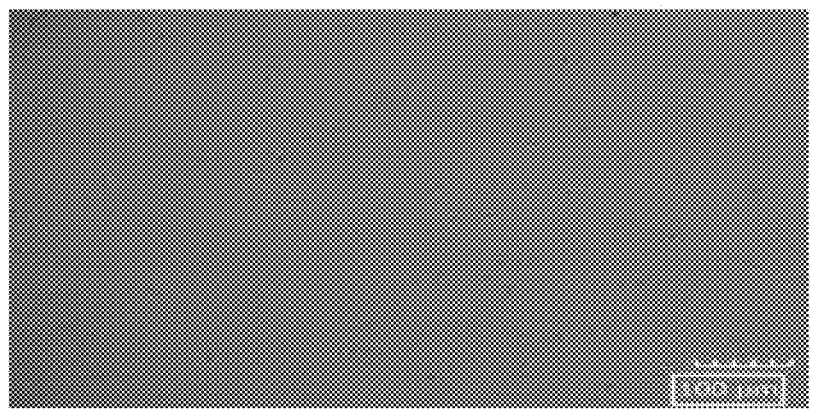
FIG. 4 is an optical microscope image of Test Example 2.

FIGS. 1 and 2 show optical microscope images of Test Examples 3 and 5, and FIGS. 3 and 4 show optical microscope images of Test Examples 1 and 2. In FIGS. 1 and 2, there existed liquid droplets containing the component (B) dispersed in a liquid skin external composition in a liquid-liquid dispersion form containing the component (C) as the main component. In FIGS. 3 and 4, the component (B) was completely dissolved in a liquid comprising the component (C) as the main component. Thus, the liquid droplets containing the component (B) were absent, and the presence of liquid droplets or precipitates was not observed even after a lapse of 30 seconds.

(Polarizing Microscopic Observation)

The nanofiber deposit was placed on a glass slide. A glass cover was placed thereon. The component (C) of Table 2 was applied from the gap between the glass slide and the glass cover. The sample was observed under a polarizing microscope within 30 seconds after the application of the aqueous medium. Liquid droplets, if any, were evaluated for their polarization characteristics and birefringence characteristics. When neither change in color nor light or dark color was found, the liquid droplets were determined as being in an amorphous state.

(Observation of Time-Dependent Change in Liquid Droplet State)

The nanofiber deposit of Example 2 was placed on a glass slide. A glass cover was placed thereon. The component (C) of Table 2 was applied from the gap between the glass slide and the glass cover. Then, the sample was observed under a polarizing microscope at a magnification of from 50× to 1 000× according to the sizes of liquid droplets to observe time-dependent change from the amorphous state to the crystal state of the liquid droplets.

The results are shown in Table 3.

TABLE 2

|  | Test Example 1 | Test Example 2 | Test Example 3 | Test Example 4 | Test Example 5 |
|---|---|---|---|---|---|
| Assembly of fiber | Example 2 | Example 4 | Example 2 | Example 4 | Example 1 |
| Component (A) polymer soluble in water and alcohol or ketone and capable of forming fibers | Polyvinylpyrrolidone (*1) | Polyvinylpyrrolidone (*1) | Polyvinylpyrrolidone (1) | Polyvinylpyrrolidone (*1) | Polyvinylpyrrolidone (*1) |
| Component (B) poorly water-soluble functional component | t-Flavanone | Ceramide (*4) | t-Flavanone | Ceramide (*4) | MA293(*3) |
| Form of nanofiber | Nanofiber deposit | Nanofiber deposit | Nanofiber deposit | Nanofiber deposit | Nanofiber deposit |
| Average fiber diameter(nm) | 1100.0 | 630.0 | 1100.0 | 630.0 | 380.0 |
| Component (C) aqueous medium — Type | Ethanol (*2) | Ethanol (*2) | Water | Water (90 Mass %)/DPG (*6) (10 Mass %) | Water |
| Component (C) aqueous medium — Content of water | 0.5 | 0.5 | 100.0 | 90.0 | 100.0 |
| Hansen solubility Log S (dissolution concentration in water) | — | — | −3.7 | — | −4.96 |
| Average particle size of liquid droplet when nanofiber was dissolved in component (C) | No liquid droplet (*5) | No liquid droplet (*5) | 20 μm | 20 μm | 10 μm |
| Confirmation of crystal/amorphous state of liquid droplet | — | — | Amorphous state | Amorphous state | Amorphous state |
| Weight of nanofiber deposit or crushed product thereof(mg) | 1.2 | 1.5 | 2.3 | 0.8 | 1.9 |
| Weight of aqueous medium(mg) | 40.0 | 43.0 | 53.0 | 21.0 | 48.0 |
| Mass (mg) of assembly of fiber/mass (mg) of aqueous medium | 0.03000 | 0.03488 | 0.04340 | 0.03810 | 0.03958 |

|  | Test Example 6 | Test Example 7 | Test Example 8 | Test Example 9 |
|---|---|---|---|---|
| Assembly of fiber | Example 3 | Example 2 | Example 2 | Example 2 |
| Component (A) polymer soluble in water and alcohol or ketone and capable of forming fibers | Polyvinylpyrrolidone (*1) | Polyvinylpyrrolidone (*1) | Polyvinylpyrrolidone (*1) | Polyvinylpyrrolidone (*1) |
| Component (B) poorly water-soluble functional component | Testosterone | t-Flavanone | t-Flavanone | t-Flavanone |
| Form of nanofiber | Nanofiber deposit | Crushed product | Crushed product | Crushed product |
| Average fiber diameter(nm) | 960.0 | 1100.0 | 1.1 | 1.1 |
| Component (C) aqueous medium — Type | Water | Water | Water | Water |
| Component (C) aqueous medium — Content of water | 100.0 | 100.0 | 100.0 | 100.0 |
| Hansen solubility Log S (dissolution concentration in water) | −1.86 | −3.7 | −3.7 | −3.7 |
| Average particle size of liquid droplet when nanofiber was dissolved in component (C) | 5 μm | 20 μm | 20 μm | 20 μm |

TABLE 2-continued

|  | | | | |
|---|---|---|---|---|
| Confirmation of crystal/amorphous state of liquid droplet | Amorphous state | Amorphous state | Amorphous state | Amorphous state |
| Weight of nanofiber deposit or crushed product thereof(mg) | 2.0 | 1.5 | 2.0 | 2.0 |
| Weight of aqueous medium(mg) | 50.0 | 42.0 | 4000.0 | 1000.0 |
| Mass (mg) of assembly of fiber/mass (mg) of aqueous medium | 0.04000 | 0.03571 | 0.00050 | 0.00200 |

|  | Test Example 10 | Test Example 11 | Test Example 12 | Test Example 13 |
|---|---|---|---|---|
| Assembly of fiber | Example 2 | Example 2 | Example 2 | Example 2 |
| Component (A) polymer soluble in water and alcohol or ketone and capable of forming fibers | Polyvinylpyrrolidone (1) | Polyvinylpyrrolidone (*1) | Polyvinylpyrrolidone (*1) | Polyvinylpyrrolidone (*1) |
| Component (B) poorly water-soluble functional component | t-Flavanone | t-Flavanone | t-Flavanone | t-Flavanone |
| Form of nanofiber | Crushed product | Crushed product | Crushed product | Crushed product |
| Average fiber diameter(nm) | 1.1 | 1.1 | 1.1 | 1.1 |
| Component (C) aqueous medium — Type | Water | Water | Water | Water |
| Component (C) aqueous medium — Content of water | 100.0 | 100.0 | 100.0 | 100.0 |
| Hansen solubility Log S (dissolution concentration in water) | −3.7 | −3.7 | −3.7 | −3.7 |
| Average particle size of liquid droplet when nanofiber was dissolved in component (C) | 20 μm | 20 μm | 20 μm | No liquid droplet |
| Confirmation of crystal/amorphous state of liquid droplet | Amorphous state | Amorphous state | Amorphous state | — |
| Weight of nanofiber deposit or crushed product thereof(mg) | 2.0 | 2.0 | 2.0 | 2.0 |
| Weight of aqueous medium(mg) | 4.0 | 2.0 | 0.7 | 40 000.0 |
| Mass (mg) of assembly of fiber/mass (mg) of aqueous medium | 0.50000 | 1.00000 | 3.00000 | 0.00005 |

*5 Dissolved, immediately thereafter, precipitated
*6 Dipropylene glycol

In Test Example 13, it is considered that liquid droplets were not to be formed because the value of mass (mg) of the assembly of fiber/mass (mg) of the aqueous medium was small, i.e., the content ratio of the poorly water-soluble component was small.

TABLE 3

| Elapsed time [sec] | State of liquid droplet |
|---|---|
| 15 | Only amorphous liquid droplets were observed |
| 50 | Only amorphous liquid droplets were observed |
| 150 | Many amorphous liquid droplets were observed with a slight amount of crystals |
| 1 500 | Amorphous liquid droplets and crystals were observed to the same extent |
| 10 000 | Many crystals were observed with a small amount of amorphous liquid droplets |

As seen from the results described above, the assembly of fiber obtained in each of Examples immobilized the poorly water-soluble component with a fine particle size and in an amorphous state. The liquid skin external composition obtained using this assembly of fiber was excellent in applicability to the skin because the poorly water-soluble component was blended at a high concentration (in a supersaturated state) in an aqueous component.

The invention claimed is:

1. A method for applying a liquid composition to the skin, the method comprising dissolving an assembly of fiber in an aqueous medium to obtain the liquid composition,
wherein the assembly of fiber comprises:
(a) polyvinylpyrrolidone; and
(b) a poorly water-soluble component,
wherein
the component (a) is present at 50 mass % or more and 98 mass % or less with respect to a total mass of the assembly of fiber,
the component (b) is present at 2 mass % or more and 40 mass % or less with respect to a total mass of the assembly of fiber, and
the component (b) which is originally crystalline is present in an amorphous state in the fiber.

2. The method for applying a liquid composition to the skin according to claim 1, wherein the assembly of fiber is dissolved in the aqueous medium by applying the aqueous medium to skin surface and applying the assembly of fiber thereonto.

3. The method for applying a liquid composition to the skin according to claim 1, wherein the assembly of fiber is dissolved into the aqueous medium to obtain a liquid composition, and the liquid composition is applied to the skin.

4. The method for applying a liquid composition to the skin according to claim 1, wherein the liquid composition is applied to the skin in 0 minutes or longer and 180 minutes or shorter, from the dissolution of the assembly of fiber in the aqueous medium.

5. The method for applying a liquid composition to the skin according to claim 1, wherein a particle size of the component (b) in the fiber is 0.1 nm to 10 nm.

6. The method for applying a liquid composition to the skin according to claim 1, further comprising electrospinning the liquid composition comprising (a) polyvinylpyrrolidone and (b) the poorly water-soluble component.

7. The method for applying a liquid composition to the skin according to claim 1, wherein the component (b) is at least one selected from the group consisting of amphipathic lipids, lipophilic vitamins, phytosterols, hexylresorcinol, glycyrrhetinic acid and derivatives thereof, salicylic acid and derivatives thereof, steroids and derivatives thereof, and ubiquinone and derivatives thereof.

8. The method for applying a liquid composition to the skin according to claim 1, wherein the component (b) is at least one selected from the group consisting of a polyphenol compound, a ceramide, a lipophilic vitamin, a phytosterol, glycyrrhetinic acid or a derivative thereof, and a steroid or a derivative thereof.

9. The method for applying a liquid composition to the skin according to claim 8, wherein the component (b) is a polyphenol compound, which is a flavonoid compound.

10. The method for applying a liquid composition to the skin according to claim 9, wherein the flavonoid compound is at least one selected from the group consisting of flavones, isoflavones, coumarin, chromone, dicumarol, chromanone, chromanol, and their isomers and derivatives, and ellagic acid.

11. The method for applying a liquid composition to the skin according to claim 8, wherein the component (b) is a ceramide having a sphingosine or phytosphingosine skeleton to which fatty acid, α-hydroxylic acid or ω-hydroxylic acid is bonded through an amide bond.

12. The method for applying a liquid composition to the skin according to claim 11, wherein the ceramide is (2S, 3R)-2-octadecanoylaminooctadecane-1,3-diol or N-2-hydroxystearoylphytosphingosine.

13. The method for applying a liquid composition to the skin according to claim 8, wherein the component (b) is a lipophilic vitamin, which is at least one selected from the group consisting of retinol, α-carotene, β-carotene, γ-carotene, cryptoxanthin, vitamin D, tocopherol, and derivatives thereof.

14. The method for applying a liquid composition to the skin according to claim 8, wherein the component (b) is a phytosterol, which is at least one selected from the group consisting of β-sitosterol, campesterol, brassicasterol, δ-5-avenasterol, lupeol, α-spinasterol, and stigmasterol.

15. The method for applying a liquid composition to the skin according to claim 8, wherein the component (b) is hexylresorcinol.

16. The method for applying a liquid composition to the skin according to claim 8, wherein the component (b) is at least one selected from the group consisting of β-glycyrrhetinic acid, glycerin glycyrrhetinate, and stearyl glycyrrhetinate.

17. The method for applying a liquid composition to the skin according to claim 8, wherein the component (b) is at least one selected from the group consisting of salicylic acid, methyl salicylate, and salicylamide.

18. The method for applying a liquid composition to the skin according to claim 8, wherein the component (b) is a steroid, which is at least one selected from the group consisting of estrogen, progesterone, testosterone, dehydroepiandrosterone, prednisolone, prednisone, progesterone, and pregnenolone.

19. The method for applying a liquid composition to the skin according to claim 1, wherein the liquid composition does not contain a monoterpene or a derivative thereof.

20. A method for producing a liquid skin external composition, the method comprising dissolving an assembly of fiber in an aqueous medium to obtain a liquid composition, wherein, the assembly of fiber comprises: (a) polyvinylpyrrolidone; and (b) a poorly water-soluble component,
wherein
the component (a) is present at 50 mass % or more and 98 mass % or less with respect to a total mass of the fiber assembly,
the component (b) is present at 2 mass % or more and 40 mass % or less with respect to a total mass of the fiber assembly,
a particle size of the component (b) in the fiber is 0.1 nm to 10 nm, and
the component (b) is present in an amorphous state in the fiber.

* * * * *